(12) United States Patent
Murano et al.

(10) Patent No.: US 11,596,719 B2
(45) Date of Patent: Mar. 7, 2023

(54) ADHESION PREVENTION FILM FOR MEDICAL DEVICES AND MEDICAL DEVICE

(71) Applicant: OLYMPUS CORPORATION, Hachioji (JP)

(72) Inventors: Yu Murano, Tokyo (JP); Takuya Fujihara, Tokyo (JP); Takeshi Deguchi, Tokyo (JP); Hiroaki Kasai, Tokyo (JP); Kohei Shiramizu, Kawasaki (JP)

(73) Assignee: OLYMPUS CORPORATION, Tokyo (JP)

(*) Notice: Subject to any disclaimer, the term of this patent is extended or adjusted under 35 U.S.C. 154(b) by 1235 days.

(21) Appl. No.: 16/105,285

(22) Filed: Aug. 20, 2018

(65) Prior Publication Data

US 2018/0353658 A1 Dec. 13, 2018

Related U.S. Application Data

(63) Continuation of application No. PCT/JP2017/005156, filed on Feb. 13, 2017.

(30) Foreign Application Priority Data

Feb. 22, 2016 (JP) .............................. JP2016-031151
Oct. 21, 2016 (JP) .............................. JP2016-207295

(51) Int. Cl.
*A61L 31/12* (2006.01)
*A61L 31/10* (2006.01)
(Continued)

(52) U.S. Cl.
CPC ............ *A61L 31/128* (2013.01); *A61B 18/12* (2013.01); *A61B 18/14* (2013.01);
(Continued)

(58) Field of Classification Search
CPC ......... A61L 31/128; A61B 18/12; A61F 2/06; C03C 3/00; C08K 5/00
See application file for complete search history.

(56) References Cited

U.S. PATENT DOCUMENTS

| 4,314,559 A | 2/1982 | Allen |
| 6,951,559 B1 | 10/2005 | Greep |

(Continued)

FOREIGN PATENT DOCUMENTS

| CN | 102245688 A | 11/2011 |
| CN | 102271607 A | 12/2011 |

(Continued)

OTHER PUBLICATIONS

Chinese Office Action (and English language translation thereof) dated Jun. 12, 2020 issued in Chinese Application No. 201780012095.0.

(Continued)

*Primary Examiner* — Dah-Wei D. Yuan
*Assistant Examiner* — Andrew J Bowman
(74) *Attorney, Agent, or Firm* — Holtz, Holtz & Volek PC

(57) ABSTRACT

This adhesion prevention film for medical devices is a single-layer or multilayer adhesion prevention film that is formed on the surface of a medical device. This adhesion prevention film for medical devices comprises an outermost layer that contains a plurality of conductive particles and a resin having a continuously usable temperature of 200° C. or higher. The surface of the outermost layer is provided with recesses and projections by having parts of the plurality of conductive particles exposed from the resin.

10 Claims, 3 Drawing Sheets

(51) Int. Cl.
  *A61L 31/08*   (2006.01)
  *A61B 18/14*   (2006.01)
  *A61B 18/12*   (2006.01)
  *H01B 1/22*    (2006.01)
  *B32B 27/00*   (2006.01)
  *B32B 27/18*   (2006.01)
  *A61B 18/00*   (2006.01)

(52) U.S. Cl.
  CPC ...... *A61B 18/1402* (2013.01); *A61B 18/1445* (2013.01); *A61L 31/088* (2013.01); *A61L 31/10* (2013.01); *B32B 27/00* (2013.01); *B32B 27/18* (2013.01); *H01B 1/22* (2013.01); *A61B 2018/0013* (2013.01); *A61B 2018/0063* (2013.01); *A61B 2018/00077* (2013.01); *A61B 2018/00101* (2013.01); *A61B 2018/00589* (2013.01); *A61B 2018/00595* (2013.01); *A61B 2018/00601* (2013.01); *A61B 2018/1412* (2013.01); *A61L 2420/04* (2013.01)

(56) References Cited

U.S. PATENT DOCUMENTS

| | | | |
|---|---|---|---|
| 8,295,902 B2 | 10/2012 | Salahieh et al. | |
| 8,519,505 B2 | 8/2013 | Hiroshige et al. | |
| 8,669,635 B2 | 3/2014 | Hiroshige et al. | |
| 8,814,861 B2 | 8/2014 | Nesbitt | |
| 9,963,560 B2 * | 5/2018 | Kozyuk | C08J 3/203 |
| 10,463,420 B2 | 11/2019 | Nesbitt | |
| 2002/0160193 A1 | 10/2002 | Hajmrle et al. | |
| 2004/0115477 A1 | 6/2004 | Nesbitt | |
| 2006/0167147 A1 * | 7/2006 | Asgari | A61K 9/5138 524/265 |
| 2006/0276785 A1 | 12/2006 | Asahara et al. | |
| 2007/0207186 A1 * | 9/2007 | Scanlon | A61F 2/915 623/1.42 |
| 2008/0058652 A1 * | 3/2008 | Payne | A61B 5/0215 623/1.1 |
| 2014/0336642 A1 | 11/2014 | Nesbitt | |
| 2020/0054384 A1 | 2/2020 | Nesbitt | |

FOREIGN PATENT DOCUMENTS

| | | | |
|---|---|---|---|
| JP | 56091743 | 7/1981 | |
| JP | 10095448 | 4/1998 | |
| JP | 2006288425 A | 10/2006 | |
| JP | 2007256088 A | 10/2007 | |
| JP | 2010284439 A | 12/2010 | |
| JP | 2013018112 A | 1/2013 | |
| WO | 02067274 A2 | 8/2002 | |
| WO | WO2008011223 * | 1/2008 | H01B 1/22 |
| WO | 2015060232 A1 | 4/2015 | |

OTHER PUBLICATIONS

International Search Report (ISR) (and English language translation thereof) dated Mar. 7, 2017 issued in International Application No. PCT/JP2017/005156.

* cited by examiner

ADHESION PREVENTION FILM FOR MEDICAL DEVICES AND MEDICAL DEVICE

CROSS REFERENCE TO RELATED APPLICATIONS

This application is a continuation application based on a PCT Patent Application No. PCT/JP2017/005156, filed on Feb. 13, 2017, whose priority is claimed on Japanese Patent Applications No. 2016-031151, filed Feb. 22, 2016, and No. 2016-207295, filed Oct. 21, 2016, the entire contents of which are hereby incorporated by reference.

BACKGROUND OF THE INVENTION

Field of the Invention

The present invention relates to an adhesion prevention film for medical devices and a medical device.

Description of the Related Art

In order to prevent biological tissues from adhering to the surface of medical instruments, adhesion prevention films may be coated on the surfaces of medical instruments. However, for example, in medical instruments that release high-frequency power to biological tissues, biological tissues strongly adhere to the surface of medical instruments due to denaturation of protein components and the like of biological tissues at high temperatures. For this reason, in medical instruments that release high-frequency power to biological tissues, it is strongly required to further improve adhesion prevention performance.

For example, in the technical field of a knife for cutting an adherent object such as an adhesive tape, as described in Japanese Unexamined Patent Application, First Publication No. 2013-018112, an adhesion prevention film is known, in which the first layer is made of a continuous silica, the second layer is made of discontinuous silica particles, and the third layer is made of a silicone.

SUMMARY

According to the adhesion prevention film for medical devices in the first aspect of the present invention, a single-layer or multilayer adhesion prevention film that is formed on a surface of a medical device includes an outermost layer that contains a resin having a continuously usable temperature of 200° C. or higher and a plurality of conductive particles, and a surface of the outermost layer is provided with recesses and projections formed by some of the plurality of conductive particles exposed from the resin.

Here, the "continuously usable temperature" of the resin is defined as the heat distortion temperature of the resin at 0.45 MPa load conforming according to ISO-75. "Resin having a continuously usable temperature of 200° C. or higher" is a resin having the heat distortion temperature of 200° C. or higher.

According to the adhesion prevention film for medical devices in the second aspect of the present invention, in the first aspect, the resin may include one or more resins selected from a group consisting of a silicone resin, a furan resin, a polyamide resin, an allyl resin, a polyimide resin, a PEEK (polyether ether ketone) resin, and an epoxy resin.

According to the adhesion prevention film for medical devices in the third aspect of the present invention, in the first aspect, the resin may be a silicone resin.

According to the adhesion prevention film for medical devices in the fourth aspect of the present invention, in any one of the first to third aspects, the plurality of conductive particles may include at least two conductive particle groups having different median diameters.

According to the adhesion prevention film for medical devices in the fifth aspect of the present invention, in any one of the first to fourth aspects, as a size of the recesses and projections on the surface of the outermost layer, a maximum height Rz (Sz) is 0.3 µm or more.

According to a sixth aspect of the present invention, in the adhesion prevention film for medical devices according to any one of the first to fifth aspects, the plurality of conductive particles may include: a first conductive particle group having a median diameter of 1 µm or more and 20 µm or less; and a second conductive particle group having a median diameter of 0.01 µm or more and 0.5 µm or less.

According to the seventh aspect of the present invention, in the adhesion prevention film for medical devices according to the sixth aspect, the first conductive particle group may include composite particles having a particulate base material composed of a nonconductor and a metal layer formed on a surface of the base material.

According to the adhesion prevention film for medical devices in the eighth aspect of the present invention, in any one of the first to sixth aspects, the plurality of conductive particles may include composite particles having a particulate base material composed of a nonconductor and a metal layer formed on a surface of the base material.

According to a ninth aspect of the present invention, in any one of the first to sixth aspects, the plurality of conductive particles may include one or more metals selected from a group consisting of silver, platinum, copper, nickel, and gold.

According to the tenth aspect of the present invention, in any one of the first to eighth aspects, a lowermost layer which contains silica as a main component and is in close contact with a surface of the medical device may be provided on a lower layer side of the outermost layer.

According to an eleventh aspect of the present invention, a medical device includes the adhesion prevention film for medical devices according to any one of the first to tenth aspects.

According to the adhesion prevention film for medical devices of the first to tenth aspects, even when used for a medical device that releases high-frequency power to a biological tissue, the adhesion prevention performance of biological tissues can be improved.

According to the medical device of the eleventh aspect, it is possible to improve adhesion prevention performance of biological tissues.

DETAILED DESCRIPTION OF THE PREFERRED EMBODIMENTS

Figure 1:
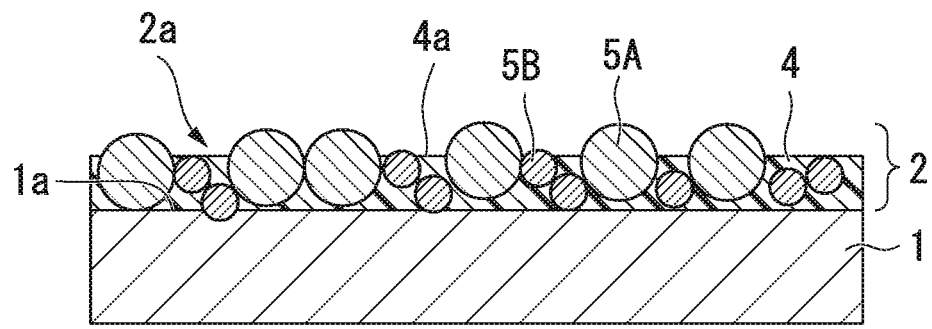
FIG. 1 is a schematic cross-sectional view showing a configuration example of an adhesion prevention film for medical devices according to a first embodiment of the present invention.

Embodiments of the present invention will be described below with reference to the accompanying drawings. In all the drawings, the same or corresponding members are denoted by the same reference numerals, and description common to them is omitted even if the embodiment is different.

First Embodiment

The adhesion prevention film for medical devices according to the first embodiment of the present invention will be described.

FIG. 1 is a schematic cross-sectional view showing a configuration example of an adhesion prevention film for medical devices according to a first embodiment of the present invention.

Since the drawings are schematic diagrams, shapes and sizes are exaggerated (the same applies to the following drawings).

FIG. 1 is a cross-sectional view illustrating a structure near a surface of a grasping portion for grasping a living body in a medical device. The grasping portion shown in FIG. 1 has a configuration of applying a high frequency to the living body grasped by the grasping portion. In the medical device, a non-insulating (conductive) adhesion prevention film 2 (an adhesion prevention film for medical devices, an outermost layer) is formed on the medical device surface portion 1 in the vicinity of the surface of the grasping portion.

The adhesion prevention film 2 of this embodiment will be described. The adhesion prevention film 2 constitutes a non-insulated part of the medical device. In the present embodiment, the adhesion prevention film 2 is a single layer.

The adhesion prevention film 2 is formed on the surface 1a of the medical device surface portion 1. Hereinafter, in the case where there is no possibility of misunderstanding, in the film thickness direction of the adhesion prevention film 2, the direction toward the surface 1a is described as an downward direction and the direction from the surface 1a toward the surface 2a (the surface of the outermost layer) opposite to the surface 1a is described as a upward direction. Terms such as lower side, lower portion, upper side, upper portion, and the like may be used corresponding to such a vertical direction.

Since FIG. 1 is an enlarged view, the state in which the adhesion prevention film 2 is formed on the entire surface 1a is drawn. However, the portion where the adhesion prevention film 2 is formed may be only a portion requiring a non-insulating portion.

The shape of the surface 1a is not particularly limited as long as the adhesion prevention film 2 can be brought into close contact. For example, the surface 1a may be a flat surface or a curved surface. In order that the adhesion prevention film 2 adheres tightly to the surface 1a, the surface 1a may be a rough surface.

Here, the rough surface means a surface having an uneven shape such as an arithmetic average roughness Ra of 0.1 μm or more and 2.0 μm or less. The arithmetic average roughness Ra may be measured by, for example, a laser microscope. The rough surface having such a surface roughness can be formed, for example, by applying a rough processing using a sandblast treatment.

The adhesion prevention film 2 includes a silicone 4, a plurality of first conductive particles 5A (a first conductive particle group), and a plurality of second conductive particles 5B (a second conductive particle group). The silicone 4 is a base resin in the adhesion prevention film 2. Each of the plurality of first conductive particles 5A and the plurality of second conductive particles 5B is a conductive particle group dispersed in the silicone 4.

The silicone 4 adheres to the surface 1a of the medical device surface portion 1. The silicone 4 holds each first conductive particle 5A and each second conductive particle 5B. The type of the silicone resin forming the silicone 4 is not particularly limited as long as the continuously usable temperature is 200° C. or higher. The continuously usable temperature of the resin is defined as the thermal deformation temperature of the resin at 0.45 MPa load conforming according to ISO-75.

As the silicone resin, for example, silicone resin SILRES (registered trademark) series for electronics (trade name; manufactured by Asahi Kasei Wacker Silicone Co., Ltd.) or the like may be used.

In the adhesion prevention film 2, a silicone resin having high heat resistance is used as a base resin, so particularly good performance can be obtained as an adhesion prevention film for medical devices to which a high frequency is applied from a non-insulating portion. However, the base resin used for the adhesion prevention film 2 is not limited to silicone resin as long as the base resin has high heat resistance.

For example, various kinds of resins having a continuously usable temperature of 200° C. or higher may be used as the base resin in the adhesion prevention film 2. The base resin may include one or more resins selected from the group consisting of, for example, silicone resin, furan resin, polyamide resin, allyl resin, polyimide resin, PEEK resin, epoxy resin.

The plurality of first conductive particles 5A and the plurality of second conductive particles 5B impart conductivity to the adhesion prevention film 2. A part of the plurality of first conductive particles 5A and the plurality of second conductive particles 5B is exposed to the outside from the surface 4a of the silicone 4 so that the surface 2a of the adhesion prevention film 2 has an uneven shape form.

However, the median diameter of the first conductive particle group constituted by the plurality of first conductive particles 5A as a whole and the median diameter of the second conductive particle group constituted by the plurality of first conductive particles 5B as a whole is different from each other. In the present embodiment, the median diameter of the first conductive particle group is larger than the median diameter of the second conductive particle group.

Since the median diameter of the first conductive particle group is larger than the median diameter of the second conductive particle group, the second conductive particles 5B easily enter the gaps between the first conductive particles 5A. The second conductive particles 5B which have entered the gaps between the adjacent first conductive particles 5A or between the first conductive particles 5A and the surface 1a are easy to contact with the first conductive particles 5A or the surface 1a. Since the second conductive particles 5B are brought into contact with the first conductive particles 5A, the contact area between the conductors in the adhesion prevention film 2 and the conductive paths increase. Since the second conductive particles 5B are brought into contact with the surface 1a, the contact area between the surface 1a and the conductor and the contact between the surface 1a and the conductive path inside the adhesion prevention film 2 increase. Therefore, the conductivity between the first conductive particles 5A/the second conductive particles 5B and the surface 1a in the adhesion prevention film 2 is improved. As a result, the volume resistivity of the adhesion prevention film 2 decreases.

Furthermore, when the second conductive particles 5B enter the gaps between the adjacent first conductive particles 5A or between the first conductive particles 5A and the surface 1a, the first conductive particles 5A are strongly supported. Therefore, the stability of the position of the first conductive particles 5A is improved.

For example, the median diameter of the first conductive particle group may be 1 μm or more and 20 μm or less. For example, the median diameter of the second conductive particle group may be 0.01 μm or more and 0.5 μm or less.

Here, the median diameter means the 50% particle diameter (D50) in the volume-based cumulative particle size distribution.

As means for measuring the particle size distribution, a light scattering type particle size analyzer is used. Specifically, depending on the distribution range of the particle size of the measurement target, for example, a Microtrack particle size analyzer based on a laser diffraction/scattering method, a Nanotrac particle size analyzer based on a dynamic light scattering method, and the like can be appropriately used.

The materials of the first conductive particles 5A and the second conductive particles 5B are not particularly limited as long as they are biocompatible and can provide necessary conductivity for the non-insulating portion. The first conductive particles 5A and the second conductive particles 5B may be metal particles. The first conductive particles 5A and the second conductive particles 5B may be particles in which metal coating is applied to the surface of the non-conductive particles.

The metals used for the first conductive particles 5A and the second conductive particles 5B may be the same metal or different metals.

Examples of the metal material that can be used for the first conductive particles 5A and the second conductive particles 5B include silver, platinum, copper, nickel, gold and the like.

In the present embodiment, each of the first conductive particles 5A and the second conductive particles 5B is composed of gold particles. The gold particle is particularly preferable as a metal material used for the first conductive particle 5A or the second conductive particle 5B in that it is excellent in biocompatibility and electric conductivity.

As the mixing amount of the first conductive particles 5A and the second conductive particles 5B in the adhesion prevention film 2, an appropriate value may be used by which the impedance required for the non-insulating portion of the medical device is satisfied and peeling of the cut or sealed biological tissue becomes easier.

For example, when the mixing amount of the first conductive particles 5A increases, the uneven shape on the surface 2a is governed by the protrusion amount of the first conductive particles 5A, so that the unevenness on the surface 2a increases. For this reason, the adhesion of biological tissues decreases. The biological material tends to peel off easily. On the other hand, when the mixing amount of the first conductive particles 5A increases, the mixing amount of the second conductive particles 5B is relatively reduced. Therefore, the number of the second conductive particles 5B interposed between the first conductive particles 5A and between the first conductive particles 5A and the surface 1a decreases. The conductivity of the adhesion prevention film 2 is reduced.

On the contrary, when the mixing amount of the second conductive particles 5B is increased, the conductivity of the adhesion prevention film 2 is improved by the second conductive particles 5B. However, since the uneven shape of the surface 2a is governed by the protrusion amount of the second conductive particles 5B, unevenness on the surface 2a are reduced. The surface 2a approaches a smooth flat surface. Therefore, the adhesion between the biological tissue and the surface 2a is enhanced, and the biological tissue is less likely to peel off.

The peeling performance due to such an uneven shape is determined by the magnitude of the maximum height Rz (Sz) of the uneven shape.

For example, as the size of the recesses and projections of the surface 2a, the maximum height Rz (Sz) may be 0.3 m or more.

In order to form the adhesion prevention film 2 having such a configuration, first, a coating material for forming the adhesion prevention film 2 is prepared. The coating material is prepared by mixing a silicone resin to be silicone 4, a solvent dissolving the silicone resin, first conductive particles 5A, and second conductive particles 5B. Thereafter, the paint is coated on the surface 1a of the medical device surface portion 1.

The coating method is not particularly limited, and an appropriate coating method is used according to the shape of the medical device surface portion 1 and the like. Examples of the coating method include spin coating, screen printing, inkjet printing, flexographic printing, spray coating, gravure printing, hot stamping, dip coating and the like.

However, if necessary, the surface 1a may be roughened by roughening the surface 1a before coating.

After coating film, the coating layer is heated and dried. When the solvent volatilizes, the silicone resin solidifies. The layer thickness of the coating layer decreases and a layer film of silicone 4 is formed. As a result, a part of the first conductive particles 5A and the second conductive particles 5B in the upper part are exposed to the outside from the surface 4a. The first conductive particles 5A and the second conductive particles 5B that face the surface 1a are in contact with the surface 1a.

Thus, the adhesion prevention film 2 is manufactured.

As shown in FIG. 1, the adhesion prevention film 2 of the present embodiment is fixed on the surface 1a by the silicone 4 being in close contact with the surface 1a of the medical device surface portion 1.

Inside the adhesion prevention film 2, many first conductive particles 5A and second conductive particles 5B are in contact with each other and are dispersed in the silicone 4. The first conductive particles 5A and the second conductive particles 5B are held by the solidified silicone 4, and the relative positions of the first conductive particles 5A and the second conductive particles 5B are fixed.

At the boundary between the surface 1a and the adhesion prevention film 2, the first conductive particles 5A and the second conductive particles 5B opposed to the surface 1a are in contact with the surface 1a.

Part of the first conductive particles 5A and the second conductive particles 5B is exposed from the surface 4a of the silicone 4. For this reason, on the surface 2a of the adhesion prevention film 2, uneven shape is formed by the first conductive particles 5A and the second conductive particles 5B.

With such a configuration, since the first conductive particles 5A and the second conductive particles 5B on the surface of the medical device surface portion 1 and the adhesion prevention film 2 are electrically connected, the adhesion prevention film 2 has conductivity as a whole.

In a medical device having a non-insulating portion, when discharging high-frequency power from a non-insulating portion, a biological tissue formed by denaturing the living tissue in contact with the non-insulating portion tends to adhere.

However, on the surface 2a of the adhesion prevention film 2 which is a non-insulating portion in the medical device of this embodiment, uneven shape is formed by gold particles. Therefore, the adhesion force of the biological tissue on the surface 2a of the adhesion prevention film 2 is lower than in the case where it is uniformly adhered to the entire surface like a smooth surface. Therefore, even if the biological tissue adheres to the surface 2a, it is easily peeled off by a small external force.

As described above, according to the adhesion prevention film 2 of the present embodiment, since the first conductive particles 5A and the second conductive particles 5B are exposed on the surface 2a to form recesses and projections, it is possible to improve the adhesion prevention performance of the biological tissue even if it is used for medical devices which releases the high frequency power to the biological tissue.

Second Embodiment

Next, the adhesion prevention film for medical devices according to the second embodiment of the present invention will be described.

Figure 2:
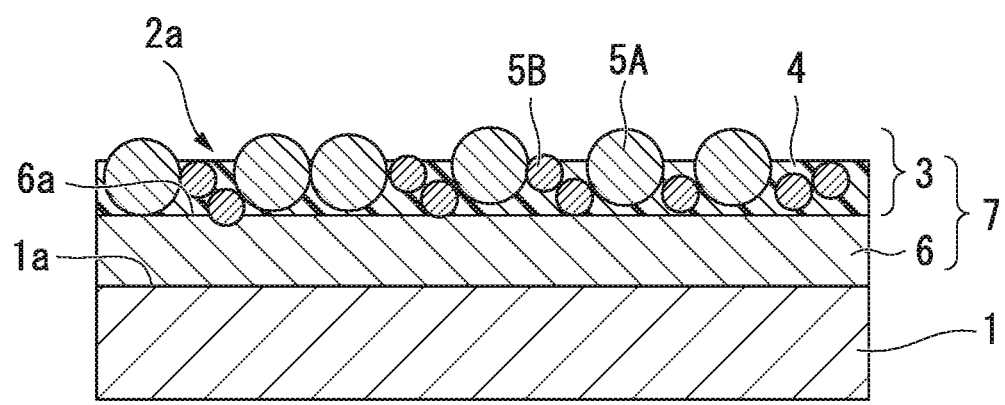
FIG. 2 is a schematic cross-sectional view showing a configuration example of an adhesion prevention film for medical devices according to a second embodiment of the present invention.

FIG. 2 is a schematic cross-sectional view showing a configuration example of an adhesion prevention film for medical devices according to a second embodiment of the present invention.

As shown in the cross-sectional configuration of FIG. 2, the non-insulating portion of the medical device is formed by replacing the adhesion prevention film 2 in the first embodiment with an adhesion prevention film 7 (adhesion prevention film for medical devices).

The adhesion prevention film 7 is composed of two layers, a first layer 6 (lowermost layer) and a second layer 3 (outermost layer). The first layer 6 is formed on the surface 1a of the medical device surface portion 1. The second layer 3 is formed on the upper surface 6a of the first layer 6.

The first layer 6 is provided to improve the adhesion of the adhesion prevention film 7 to the surface 1a.

As the material of the first layer 6, an appropriate material having excellent adhesion to the second layer 3 and the surface 1a is used. In the present embodiment, since the base resin of the second layer 3 described later is made of a silicone resin, a silica layer containing silica as a main component is adopted as the first layer 6. In order to form the silica layer, for example, a coating agent such as Olam (registered trademark) glass coat series (trade name; manufactured by Art Bleed Co., Ltd.) may be used.

The layer thickness of the first layer 6 can be set to an appropriate layer thickness according to the necessity of adhesion strength, durability, and the like. For example, the layer thickness of the first layer 6 may be 0.1 μm or more and 10 μm or less.

In the present embodiment, the second layer 3 is configured similarly to the adhesion prevention film 2 of the first embodiment. Therefore, the base resin of the second layer 3 in this embodiment is the silicone 4.

However, as in the first embodiment, the base resin of the second layer 3 may be replaced with a resin other than silicone resin having a continuously usable temperature of 200° C. or higher.

In order to form the adhesion prevention film 7 having such a constitution, the second layer 3 is formed after the first layer 6 is formed on the surface 1a of the medical device surface portion 1.

In order to form the first layer 6, for example, a coating solution containing silica in a solvent is coated on the surface 1a of the medical device surface portion 1 and then heated and dried.

As in the case of the first embodiment, when roughening the surface 1a, by making the layer thickness of the first layer 6 sufficiently thin compared to the amount of unevenness of the roughened processing, it is possible to form an uneven shape also on the upper surface 6a of the first layer 6.

The second layer 3 is formed in the same manner as the adhesion prevention film 2 of the first embodiment except that it is formed on the first layer 6.

According to the adhesion prevention film 7 of the present embodiment, since the second layer 3 similar to the adhesion prevention film 2 of the first embodiment is provided as the outermost layer, it is possible to improve adhesion prevention performance of biological tissues similarly to the first embodiment even when used for medical device that releases high frequency power.

Furthermore, according to the adhesion prevention film 7, the first layer 6 is formed between the second layer 3 and the surface 1a of the medical device surface portion 1. Since the first layer 6 is made of a silica layer, it has good adhesion to the metal medical device surface portion 1. Since the first layer 6 is formed of a silica layer, the adhesion to the silicone 4 of the second layer 3, the first conductive particles 5A, and the second conductive particles 5B is also good.

Therefore, according to the adhesion prevention film 7, the adhesion strength of the second layer 3 can be improved as compared with the case where the second layer 3 is directly formed on the surface 1a. Therefore, according to the adhesion prevention film 7, it is possible to further improve the durability and reliability of the medical device.

Third Embodiment

Next, the adhesion prevention film for medical devices according to the third embodiment of the present invention will be described.

Figure 3:
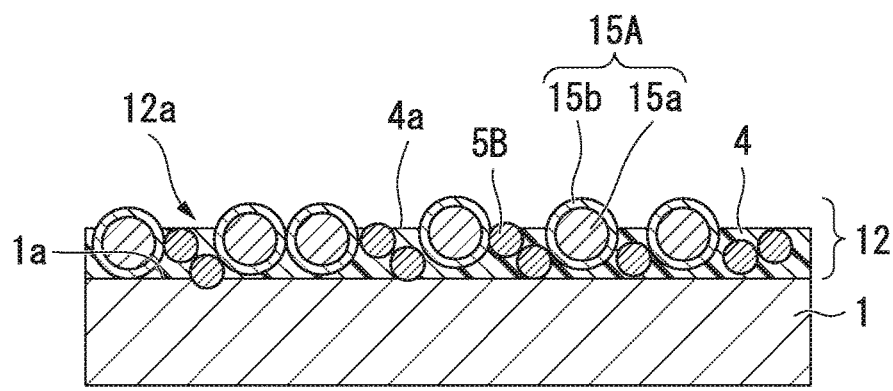
FIG. 3 is a schematic cross-sectional view showing a configuration example of an adhesion prevention film for medical devices according to a third embodiment of the present invention.

FIG. 3 is a schematic cross-sectional view showing a configuration example of an adhesion prevention film for medical devices according to a third embodiment of the present invention.

The adhesion prevention film 12 (adhesion prevention film for medical device) of the present embodiment includes the first conductive particles 15A instead of the first conductive particles 5A in the adhesion prevention film 2 of the first embodiment. The whole of the first conductive particles 15A constitutes a first conductive particle group. The median diameter of the first conductive particle group in the present embodiment is the same as the median diameter of the first conductive particle group in the first embodiment.

Hereinafter, differences from the first embodiment will be mainly described.

The first conductive particles 15A are composite particles having a particulate base material 15a composed of a nonconductor and a metal layer 15b formed on the surface of the base material 15a.

The material of the base material 15a is not limited as long as it is a nonconductor. It is more preferable that the material of the base material 15a has good heat insulating properties. The base material 15a may have a hollow structure. The hollow structure may be a spherical shell structure or a porous structure. When the base material 15a has a hollow structure, the heat insulating property of the first conductive particles 15A is improved as compared with the case where the base material 15a is a solid body.

As the material of the base material 15a, for example, glass, silica, alumina, zirconia or the like can be used. Hollow silica type particles, hollow glass balls, or the like may be used as the base material 15a. Specific examples of hollow glass spheres include 3M (registered trademark) glass bubbles (trade name; manufactured by 3M Co., Ltd.) and the like.

The content of the first conductive particles 15A in the adhesion prevention film 12 may be an amount in which the size of the unevenness of the surface 2a is 0.3 μm or more in the maximum height Rz (Sz) as in the first embodiment.

As the metal material used for the metal layer 15b, for example, silver, platinum, copper, nickel, gold and the like can be mentioned like the first conductive particles 5A in the first embodiment. The metal material used for the metal layer 15b may be the same as or different from the metal material used for the second conductive particles 5B.

The layer thickness of the metal layer 15b is not particularly limited as long as necessary conductivity and durability of the adhesion prevention film 12 can be secured. For example, since the specific surface area of the sphere is inversely proportional to the diameter size, it is also good that the layer thickness of the metal layer 15b is be selected to be thinner (thicker) as the particle size of the base material 15a becomes smaller (larger).

The metal layer 15b may be formed on the base material 15a by an appropriate coating. Examples of the coating method that can be used for forming the metal layer 15b include electroless plating, PVD (Physical Vapor Deposition), CVD (Chemical Vapor Deposition), and the like. Examples of PVD include sputtering, vapor deposition and the like.

The adhesion prevention film 12 having such a structure is formed on the medical device surface portion 1 in the same manner as the adhesion prevention film 2 in the first embodiment.

The adhesion prevention film 12 is configured similarly to the prevention film 2 except that the first conductive particles 15A are used instead of the first conductive particles 5A of the adhesion prevention film 2 of the first embodiment. Therefore, according to the adhesion prevention film 12 of the present embodiment, it is possible to improve adhesion prevention performance of a biological tissue even when used for medical devices that releases high-frequency power to a biological tissue as in the first embodiment.

Since the metal layer 15b is formed on the surface of the base material 15a in the first conductive particles 15A in the present embodiment, the amount of the use of a metal is reduced compared with the first conductive particles 5A in the first embodiment. The nonconductor used for the base material 15a is inexpensive as compared with the metal material. When the first conductive particles 15A have the same diameter as the first conductive particles 5A, the used amount of expensive metal material is reduced in the first conductive particles 15A compared to the first conductive particles 5A. Therefore, the component cost of the first conductive particles 15A is reduced. In particular, when an expensive material such as gold or platinum is used as the base material 15a, the effect of reducing the parts cost increases.

Furthermore, in the present embodiment, since the first conductive particles 15A are composed of a composite of a metal material and a nonconductor material, the thermal conductivity of the first conductive particles 15A is lower than that of metal particles having the same diameter. Therefore, by including the first conductive particles 15A in the adhesion prevention film 12, the heat insulating property of the adhesion prevention film 12 is improved.

For example, when the adhesion prevention film 12 is used for the surface of the electrode portion of the medical device which releases the high frequency power to the living tissue (biological tissue), the electrode portion becomes high temperature due to Joule heat caused by high frequency power. When the temperature of the electrode portion itself becomes high, even if the living tissue in contact with the surface of the electrode portion is excessively denatured, the living tissue may be easily attached to the electrode portion.

However, in the present embodiment, by including the first conductive particles 15A on the surface of the medical device which is in contact with the living body, the adhesion prevention film 12 having a higher heat insulating property than the case where only the metal particles are contained is formed. Therefore, according to the adhesion prevention film 12, it is possible to prevent the biological tissue from being excessively denatured by the good heat insulating performance of the adhesion prevention film 12. As a result, adhesion prevention performance of the adhesion prevention film 12 is further improved.

Fourth Embodiment

Next, a medical device according to a fourth embodiment of the present invention will be described.

Figure 4:
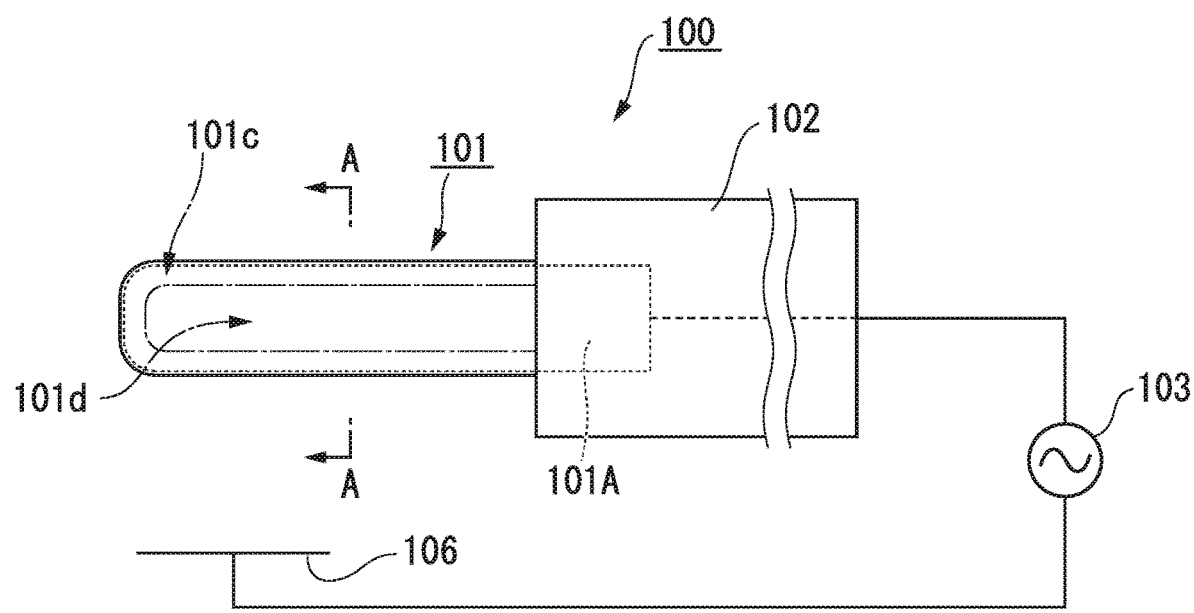
FIG. 4 is a schematic configuration diagram showing an example of a medical device according to a fourth embodiment of the present invention.
Figure 5:
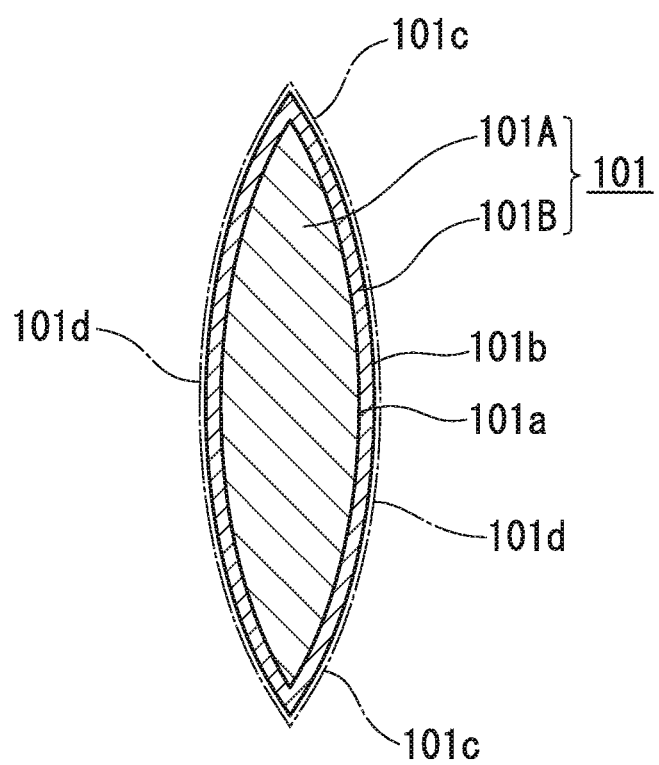
FIG. 5 is a sectional view taken along the line AA in FIG. 4.

FIG. 4 is a schematic configuration diagram showing an example of the medical device according to the fourth embodiment of the present invention. FIG. 5 is a cross-sectional view taken along line AA in FIG. 4.

The high frequency knife 100 of the present embodiment shown in FIG. 4 is an example of the medical device of the present embodiment.

The high-frequency knife 100 is a medical treatment tool that performs treatment on a living tissue (biological tissue) by applying a high frequency voltage. For example, the high-frequency knife 100 can cut or resect a living tissue, coagulate (hemostasis) a living tissue, or cauterize the living tissue.

The high-frequency knife 100 includes a bar-shaped grasping portion 102 for the operator to hold with the hand and an electrode portion 101 protruding from the distal end of the grasping portion 102.

The electrode unit 101 is brought into contact with the living tissue as the treatment target to apply a high-frequency voltage. As shown in FIG. 5, the electrode portion 101 includes a metallic electrode main body 101A and an adhesion prevention film 101B (medical device adhesion prevention film).

As shown in FIG. 4, the outer shape of the electrode main body 101A is a rectangular piece having a rounded corner portion at the tip in the projecting direction. As shown in FIG. 5, the outer shape of the electrode main body 101A has a flat shape in which the thickness decreases toward the outer edge in a cross section orthogonal to the protruding direction. Although not specifically shown, the cross-sectional shape of the electrode main body 101A at the tip portion in the projecting direction likewise has a thin thickness toward the outer edge.

As shown in FIG. 4, the electrode main body 101A is electrically connected to the high-frequency power supply 103 by the wiring connected to the base end portion held by the grasping portion 102. The high-frequency power source 103 is electrically connected to a counter electrode plate 106 to be mounted on the object to be treated.

As shown in FIG. 5, the adhesion prevention film 101B is a thin film provided so as to cover the electrode body surface 101a. The outer surface of the adhesion prevention film 101B constitutes the electrode surface 101b of the electrode portion 101.

On the side of the electrode surface 101b excluding the blade portion 101c, an abdominal portion 101d, which is formed in a gently curved shape or a planar shape as a whole, is formed. The abdominal portion 101d is mainly used for holding treatment subjects and performing treatment such as coagulation and cauterization.

As a material of the electrode main body 101A, an appropriate metallic material having conductivity, such as a metal or an alloy, is used. For example, an aluminum alloy, stainless steel, or the like may be used as the material of the electrode main body 101A.

The adhesion prevention film 101B has the same structure as any one of the adhesion prevention films 2, 7, and 12 in the first to third embodiments. The electrode body 101A in the present embodiment corresponds to the medical device surface portion 1 in the first to third embodiments.

Next, the operation of the high-frequency knife 100 having such a configuration will be described.

The treatment using the high-frequency knife 100 is performed, for example, in a state where the counter electrode plate 106 is attached to the patient and a high frequency voltage is applied to the electrode unit 101 by the high frequency power supply 103. The operator brings the blade portion 101c or the abdominal portion 101d of the electrode portion 101 into contact with the object to be treated such as the treated portion of the patient while applying the high-frequency voltage to the electrode portion 101.

The electrode portion 101 is covered with an adhesion prevention film 101B. First and second conductive particle groups are dispersed in the adhesion prevention film 101B. Part of the first and second conductive particle groups are exposed on the electrode surface 101b. The first and second conductive particles are brought into contact with each other and a part thereof is brought into contact with the electrode body surface 101a inside the adhesion prevention film 101B, so that a conductive path continuing in the thickness direction of the adhesion prevention film 101B is formed.

Uneven shape is formed on the electrode surface 101b of the adhesion prevention film 101B by exposing a part of the first and second conductive particles from the silicone 4 which is less likely to adhere to living tissue.

When a high frequency voltage is applied between the electrode portion 101 and the counter electrode plate 106, a high frequency current is generated via the adhesion prevention film 101B. In the contact portion between the electrode portion 101 and the living tissue, Joule heat is generated by a current having a large current density flowing from the first and second conductive particles exposed at the electrode surface 101b to the living tissue. As a result, the moisture of the living tissue of the object to be treated rapidly evaporates, and the living tissue is ruptured by the blade portion 101c. For this reason, it is possible to incise and cut the living tissue by moving the electrode unit 101 with respect to the living tissue.

When a high-frequency current is flowed in a state where the abdomen 101d is pressed against the object to be treated, moisture of the living tissue of the object to be treated rapidly evaporates. In the vicinity of the abdomen 101d, the living tissue is coagulated. Therefore, when the abdomen 101d is pressed against the object to be treated, hemostasis and cauterization of living tissue can be performed.

When the necessary treatment is completed, the surgeon separates the electrode unit 101 from the object to be treated. Since the electrode surface 101b in contact with the living tissue is formed by the adhesion prevention film 101B, the living tissue easily peels off from the electrode surface 101b when separating the electrode portion 101.

As a result, in the high-frequency knife 100, the living tissue hardly adheres to the electrode surface 101b. Therefore, according to the high-frequency knife 100, it is possible to prevent deterioration in the treatment performance during treatment. Furthermore, according to the high-frequency knife 100, the durability of the electrode unit 101 is secured even when the electrode unit 101 is repeatedly used.

As described above, according to the high-frequency knife 100, since the adhesion prevention film 101B is provided on the surface of the electrode portion 101, it is possible to improve the adhesion prevention performance of the biological tissue.

In each of the above embodiments, the case where the outermost layer is composed of the first conductive particle group and the second conductive particle group has been described. However, the plurality of conductive particle groups are not limited to the two groups. The plurality of conductive particle groups may be three or more groups.

As long as necessary concave-convex shape and conductivity are obtained according to the purpose of use of the medical device using the adhesion prevention film for medical device, only one group of conductive particles may be used.

In the above description of the second embodiment, the case where the first layer 6 is made of a silica layer containing silica as a main component has been described. However, the material of the first layer 6 is not limited to the silica layer. As a material of the first layer 6, an appropriate material may be used according to the materials of the medical device surface portion 1 and the second layer 3.

In the description of the second embodiment, the case where the adhesion prevention film 7 is a multilayer film having a two-layer structure has been described. However, the adhesion prevention film for medical device may be a multilayer film of three or more layers. In this case, the adhesion prevention film for medical device can be provided with an intermediate layer between the lowermost layer and the outermost layer. Therefore, even when there is no material having good adhesiveness to both the base material and the outermost layer of the grasping portion of the medical device, the adhesion prevention film for medical device is more firmly fixed by sandwiching an appropriate intermediate layer.

The material of the lowermost layer and the intermediate layer is not limited to a material having a homogeneous component. For example, the lowermost layer and the intermediate layer may be composed of a graded layer whose composition ratio changes in the layer thickness direction.

In the description of the third embodiment described above, an example was described in which only a first conductive particle group out of a plurality of conductive particle groups contain composite particles including a particle-like base material made of a nonconductor and a metal layer formed on the surface of the base material. However, in the third embodiment, only the second conductive particle group may contain composite particles. In the third embodiment, the first and second conductive particle groups may contain composite particles.

When three or more conductive particle groups are included in the adhesion prevention film for medical devices, at least one group out of three or more conductive particle groups may contain composite particles. In this case, composite particles may be contained only in the conductive particle group having the largest median diameter in order to efficiently reduce the parts cost and improve the heat insulating property.

EXAMPLE

Next, examples of the adhesion prevention film for medical devices of the first to third embodiments will be described together with comparative examples.

First, Examples 1 to 5 of the adhesion prevention film 2 of the first embodiment and Example 6 of the adhesion prevention film 7 of the second embodiment will be described together with Comparative Examples 1 and 2.

The compositions and evaluation results of the paints for forming the outermost layer for forming the adhesion prevention film for medical devices of each example and each comparative example are shown in the following "Table 1" and "Table 2". However, in "Table 1", the notation of the sign of each member is omitted.

TABLE 2-continued

| | EVALUATION RESULT | |
| --- | --- | --- |
| | ADHESION PREVENTION | ELECTRIC CONDUCTIVE |
| COMPARATIVE EXAMPLE 1 | ○ | X |
| COMPARATIVE EXAMPLE 2 | X | ○ |

Example 1

Example 1 is an example of the adhesion prevention film 2. The adhesion prevention film 2 of Example 1 was produced as follows.

An aluminum substrate was used as the substrate on which the adhesion prevention film 2 was formed.

In order to form the adhesion prevention film 2, a paint for forming an outermost layer mixed with 10 parts by weight of a silicone resin, 30 parts by weight of a first conductive particle, 30 parts by weight of a second conductive particle, and 30 parts by weight of a solvent was prepared.

As the silicone resin, SILRES (registered trademark) MPF 52 E (trade name; manufactured by Wacker Asahi Kasei Silicone Co., Ltd.) was used. As the first conductive particle 5A, a gold particle group (first conductive particle group) having a median diameter of 5 μm was used. As the second conductive particle 5B, a gold particle group (second conductive particle group) having a median diameter of 50 nm was used. Here, as means for measuring the particle size distribution, a Microtrack particle size analyzer based on a laser diffraction/scattering method was used for the measurement of the first conductive particles, and a Nanotrac particle size analyzer based on a dynamic light scattering formula was used for the measurement of the second conductive particles. As a solvent, xylene was used.

This outermost layer forming coating material was coated on an aluminum substrate by dip coating and dried at a temperature condition of 200° C. for 1 hour. As a result, an adhesion prevention film 2 having a film thickness of 5.0 μm was formed.

The maximum height Rz (Sz) of the surface 2a of the adhesion prevention film 2 was 3.5 μm as measured by a laser microscope OLS-3500 (trade name; manufactured by Olympus Corporation).

TABLE 1

| | | COMPOSITION OF COATING FOR FORMING OUTERMOST LAYER | | | | | | | SURFACE OF |
| --- | --- | --- | --- | --- | --- | --- | --- | --- | --- |
| | | SILICONE | SECOND CONDUCTING PARTICLE | | | FIRST CONDUCTING PARTICLE | | | SOL- | OUTERMOST LAYER |
| | SILICA LAYER | RESIN pts. wt. | QUALITY OF MATERIAL | MEDIAN DIAMETER (nm) | pts. wt. | QUALITY OF MATERIAL | MEDIAN DIAMETER (μm) | pts. wt. | VENT pts. wt. | MAXIMUM HEIGHT Rz(μm) |
| EMBODIMENT 1 | X | 10 | GOLD | 10 | 30 | GOLD | 5 | 30 | 30 | 3.5 |
| EMBODIMENT 2 | X | 10 | GOLD | 50 | 30 | GOLD | 1 | 30 | 30 | 0.7 |
| EMBODIMENT 3 | X | 10 | GOLD | 50 | 30 | GOLD | 5 | 50 | 30 | 3.0 |
| EMBODIMENT 4 | X | 10 | GOLD | 50 | 30 | GOLD | 20 | 30 | 30 | 15.1 |
| EMBODIMENT 5 | X | 10 | GOLD | 500 | 30 | GOLD | 5 | 30 | 30 | 3.3 |
| EMBODIMENT 6 | ○ | 10 | GOLD | 50 | 30 | GOLD | 5 | 30 | 30 | 3.6 |
| COMPARATIVE EXAMPLE 1 | X | 10 | — | — | — | GOLD | 10 | 60 | 30 | 7.5 |
| COMPARATIVE EXAMPLE 2 | X | 10 | GOLD | 50 | 60 | — | — | — | 30 | 0.2 |

TABLE 2

| | EVALUATION RESULT | |
| --- | --- | --- |
| | ADHESION PREVENTION | ELECTRIC CONDUCTIVE |
| EMBODIMENT 1 | ○ | ○ |
| EMBODIMENT 2 | ○ | ○ |
| EMBODIMENT 3 | ○ | ○ |
| EMBODIMENT 4 | ○ | ○ |
| EMBODIMENT 5 | ○ | ○ |
| EMBODIMENT 6 | ○ | ○ |

Examples 2 to 5

Examples 2 to 5, as shown in Table 1, were constructed in the same way as in Example 1 except that the median diameter of at least one of the first conductive particles 5A and the second conductive particles 5B is different from that in Example 1.

In Examples 2 to 4, the median diameters of the second conductive particles 5B were all 50 nm, and the median diameters of the first conductive particles 5A were 1 μm, 5 μm, and 20 μm, respectively.

Example 5 was constructed in the same manner as in Example 1 except that the median diameter of the second conductive particles 5B was 500 nm.

The maximum height Rz (Sz) of the surface 2a of the adhesion prevention film 2 of Examples 2 to 5 was measured in the same manner as in Example 1 and found to be 0.7 μm, 3.0 μm, 15.1 μm, and 3.3 μm.

Example 6

Example 6 is an example of the adhesion prevention film 7. In Example 6, a silica layer was provided as the first layer 6. In Example 6, the second layer 3 was configured in the same manner as the adhesion prevention film 2 of Example 3 described above.

The adhesion prevention film 7 of Example 6 was produced as follows.

First, Olam (registered trademark) 60 (trade name; manufactured by Art Bleed Co.) was applied by spin coating to the surface of the same aluminum substrate as in Example 1. After this, the coating film was dried at 200° C. for 1 hour. As a result, a silica layer having a layer thickness of 1.0 μm was formed. Thereafter, the outermost layer-forming coating material for forming the second layer 3 was coated on the silica layer in the same manner as in Example 1 described above. The coating film of the outermost layer forming coating material was dried at a temperature condition of 200° C. for 1 hour. As a result, the second layer 3 having a layer thickness of about 4.6 μm was formed.

The maximum height Rz (Sz) of the surface 2a of the adhesion prevention film 7 of Example 6 was measured in the same manner as in Example 1 and found to be 3.6 μm.

Comparative Examples 1 and 2

As shown in Table 1, the adhesion prevention film for medical device of Comparative Example 1 was prepared in the same manner as in Example 1, except that 60 parts by weight of gold particles having a median diameter of 10 μm were provided instead of the first conductive particles 5A and the second conductive particles 5B were deleted.

The adhesion prevention film for medical device of Comparative Example 2 was prepared in the same manner as in Example 1, except that 60 parts by weight of gold particles having a median diameter of 50 nm was provided instead of the second conductive particles 5B and the first conductive particles 5A were deleted.

The maximum height Rz (Sz) of the surface 2a of the adhesion prevention film for medical devices of Comparative Examples 1 and 2 was measured in the same manner as in Example 1, and it was 7.5 μm and 0.2 μm, respectively.

[Evaluation Method]

Adherence evaluation and conductivity evaluation were carried out using the adhesion prevention films for medical devices of Examples 1 to 6 and Comparative Examples 1 and 2 as samples to be tested. Table 2 shows the evaluation results of adhesion evaluation and conductivity evaluation.

In order to evaluate the adhesion property, the sample to be tested was heated at 200° C. by a hot plate, and blood of horse was discharged as a biological tissue thereon. Thereafter, a tape peeling test by a cross cut method based on JIS K 5600-5-6 was performed on the sample to be tested.

In the adhesion evaluation, the peeled state of the solidified matter of the blood of horse in the test sample after the test was evaluated based on the classification in Table 1 described in JIS K 5600-5-6. When the peeled-off state corresponds to "classification 5", it was evaluated as no adhesion (described as "o (good)" in Table 2). When the peeled-off state was "classification 0 to 4", there was adhesion (described as "x (no good)" in Table 1).

In each of the test samples of Examples 1 to 6 and Comparative Examples 1 and 2, part or all of the adhesion prevention film for medical devices did not peel off together with the solidified product of the blood of horse.

As the conductivity evaluation, the volume resistivity of the sample to be tested was measured.

When the volume resistivity is $1.0 \times 10^8$ Ω·cm or less, the conductivity was evaluated to be good (described as "o (good)" in Table 1) and the volume resistivity exceeds $1.0 \times 10^8$ Ω·cm, it was evaluated as poor conductivity (described as "x (no good)" in Table 2).

[Evaluation Results]

According to the evaluation result of the adhesion evaluation shown in Table 2, even when blood of horse denatured in a heated state adheres, the adhesion prevention films for medical devices of Examples 1 to 6 and Comparative Example 1 become a state to be evaluated as "no adhesion" after the tape peeling test. Therefore, it can be seen that adhesion prevention performance of the biological tissue is good.

In contrast, Comparative Example 2, which does not include the first conductive particles 5A, was evaluated as "adhering", indicating that the adhesion prevention performance of the biological tissue is inferior.

Since the surface of the adhesion prevention film for medical devices of each sample to be tested has the same material, these differences are due to differences in the uneven shape of the surface formed by the first conductive particles and the second conductive particles.

In each of Examples 1 to 6 and Comparative Example 1, since the first conductive particles 5A having a median diameter of 1 μm or more and 20 μm or less were included, the irregular shape of the surface of the adhesion prevention film for medical devices was such that the maximum height Rz (Sz) was 0.7 μm to 15.1 μm as described above.

On the other hand, since the median diameter of the second conductive particles 5B in Comparative Example 2 was 50 nm, the second conductive particles 5B were only exposed on the surface, so the irregular shape of the surface of the adhesion prevention film for medical devices was such that the maximum height Rz (Sz) was 0.2 μm. As described above, it is considered that the adhesion prevention film of Comparative Example 2 has a smooth surface close to a flat surface, so that adhesion with a biological tissue is strengthened.

According to the evaluation result of the conductivity evaluation shown in Table 2, the adhesion prevention films for medical devices of Examples 1 to 6 and Comparative Example 2 had good conductivity.

In contrast, in Comparative Example 1 not including the second conductive particles 5B, the conductivity was poor.

In Examples 1 to 6 in which the first conductive particles 5A and the second conductive particles 5B are mixed, the first conductive particles 5A are in contact with each other. Furthermore, in Examples 1 to 6, the second conductive particles 5B having a small diameter enter the gaps between the first conductive particles 5A or between the first conductive particles 5A and the aluminum substrate. Therefore, it is considered that the conductivity was improved by filling the second conductive particles 5B in these gaps.

In Comparative Example 1, since the second conductive particles 5B are not included, conduction occurs only at a contact point between the first conductive particles 5A or a contact point between the first conductive particles 5A and the aluminum substrate. As a result, in Comparative Example 1, since the substantial contact area is smaller than those of Examples 1 to 6 and Comparative Example 2, the electric resistance is considered to be large.

Examples 7 and 8 of the adhesion prevention film 12 of the third embodiment and examples 9 and 10 of the adhesion prevention film combining the second and third embodiments will be described.

Table 3 below shows the formulation composition of the outermost layer forming paint for forming the adhesion prevention film for medical devices of Examples 7 to 10. However, in Table 3, notation of the reference numerals of each member is omitted.

the metal layer 15b was 0.5 μm. The median diameter of the first conductive particles 15A in this example was 20 μm.

Example 8 is the same as Example 7 except that the material and median diameter of the second conductive particles 5B are changed and the material of the first conductive particles 15A is changed.

Platinum was used as the material of the second conductive particles 5B in this example. The median diameter of the second conductive particles 5B of this example was 500 nm.

The maximum height Rz (Sz) of the surface 12a of the adhesion prevention film 12 in Examples 7 and 8 was measured in the same manner as in Example 1 and found to be 16.5 μm and 14.1 μm, respectively.

Examples 9 and 10

In Examples 9 and 10, a first layer 6 similar to that of Example 6 is provided.

In Example 9, in place of the second layer 3 of Example 6, a layer film was provided having a structure similar to that of the adhesion prevention film 12 of Example 8 except that the material and median diameter of the first conductive particles 15A were changed. Zirconia and platinum were used as the base material 15a and the metal layer 15b of the first conductive particles 15A in the present example. The

TABLE 3

| | | COMPOSITION OF COATING FOR FORMING OUTERMOST LAYER | | | | |
|---|---|---|---|---|---|---|
| | SILICA LAYER | SILICONE RESIN pts. wt. | SECOND CONDUCTING PARTICLE | | | FIRST CONDUCTING PARTICLE BASE |
| | | | QUALITY OF MATERIAL | MEDIAN DIAMETER (nm) | pts. wt. | |
| EMBODIMENT 7 | X | 10 | GOLD | 10 | 30 | HOLLOW SILICA |
| EMBODIMENT 8 | X | 10 | PLATINUM | 500 | 30 | SILICA |
| EMBODIMENT 9 | ○ | 10 | PLATINUM | 500 | 30 | ZIRCONIA |
| EMBODIMENT 10 | ○ | 10 | GOLD | 10 | 30 | ALUMINA |

| | COMPOSITION OF COATING FOR FORMING OUTERMOST LAYER | | | | | SURFACE OF OUTERMOST LAYER |
|---|---|---|---|---|---|---|
| | FIRST CONDUCTING PARTICLE | | | | SOL-VENT pts. wt. | |
| | METAL LAYER | | MEDIAN DIAMETER (μm) | pts. wt. | | WAXIMUM HEIGHT Rz(μm) |
| | QUALITY OF MATERIAL | LAYER THICKNESS (μm) | | | | |
| EMBODIMENT 7 | GOLD | 0.5 | 20 | 30 | 30 | 16.5 |
| EMBODIMENT 8 | PLATINUM | 0.3 | 20 | 30 | 30 | 14.1 |
| EMBODIMENT 9 | PLATINUM | 0.05 | 1 | 30 | 30 | 0.31 |
| EMBODIMENT 10 | GOLD | 0.03 | 8 | 30 | 30 | 0.53 |

Examples 7, 8

Examples 7 and 8 are examples of the adhesion prevention film 12.

Example 7 was constructed in the same manner as Example 1 except that the first conductive particles 15A were used in place of the first conductive particles of Example 1 described above.

Hollow silica and gold were used as the base material 15a and the metal layer 15b of the first conductive particles 15A in the present example, respectively. The layer thickness of layer thickness of the metal layer 15b was 0.05 μm. The median diameter of the first conductive particles 15A in this example was 1 μm.

In Example 10, a layer film was provided having a structure similar to that of the adhesion prevention film 12 of Example 7, except that the material and median diameter of the first conductive particles 15A were changed in place of the second layer 3 of Example 6. Alumina and gold were used as the base material 15a and the metal layer 15b of the first conductive particles 15A in the present example, respectively. The thickness of the metal layer 15b was 0.03

µm. The median diameter of the first conductive particles 15A in this example was 1 µm.

The maximum height Rz (Sz) of the surface of the outermost layer in Examples 9 and 10 was measured in the same manner as in Example 1 and found to be 0.31 nm and 0.53 µm, respectively.

[Evaluation Results]

Adhesion evaluation and conductivity evaluation were carried out in the same manner as in Examples 1 to 6 using Examples 7 to 10. Each evaluation result is shown in the following Table 4. The meanings of the symbols indicating the evaluation results of "adhesiveness" and "conductivity" in Table 4 are the same as the meanings of the symbols in Table 2.

TABLE 4

| | EVALUATION RESULT | |
| --- | --- | --- |
| | ADHESION PREVENTION | ELECTRIC CONDUCTIVE |
| EMBODIMENT 7 | ○ | ○ |
| EMBODIMENT 8 | ○ | ○ |
| EMBODIMENT 9 | ○ | ○ |
| EMBODIMENT 10 | ○ | ○ |

As shown in Table 4, in each of the examples, the adhesion evaluation was "no adhesion" ("o" in Table 4) and the conductivity evaluation was "good" (in Table 4, "o"). Therefore, even when only the surface layer of the first conductive particles 15A has conductivity by the metal layer 15b, it is understood that good conductivity was obtained by combining with the second conductive particles 5B.

[Heat Insulation Property Evaluation]

Next, the heat insulating property evaluation in the film configuration of each embodiment will be described.

In order to evaluate the heat insulating property of each example, a test sample for evaluating heat insulating property was prepared. In the test sample for evaluating the heat insulating property, the adhesion prevention film of each of the above-described examples was formed on the surface of an aluminum plate having a thickness of 3 mm. However, in order to accurately measure the difference in heat insulating property, the film thickness of the test sample for evaluating the heat insulating property was set to 25 µm±5 µm.

Each sample to be tested was placed on a hot plate heated to 200° C. so that the hot plate and the aluminum plate of each test sample were in contact. Each test sample was heated for at least 1 minute. The temperature of the film surface 1 minute after the start of heating was measured by a surface thermometer for microscopic surface. The temperature after 1 minute is shown in the following Table 5.

TABLE 5

| | EVALUATION RESULT | |
| --- | --- | --- |
| MEMBRANE COMPOSITION | TEMPERATURE OF 1 MINUTE LATER (° C.) | HEAT INSULATION |
| EMBODIMENT 1 | 188 | ○ |
| EMBODIMENT 2 | 192 | ○ |
| EMBODIMENT 3 | 188 | ○ |
| EMBODIMENT 4 | 191 | ○ |
| EMBODIMENT 5 | 192 | ○ |
| EMBODIMENT 8 | 190 | ○ |
| EMBODIMENT 7 | 170 | ⊚ |
| EMBODIMENT 8 | 178 | ⊚ |

TABLE 5-continued

| | EVALUATION RESULT | |
| --- | --- | --- |
| MEMBRANE COMPOSITION | TEMPERATURE OF 1 MINUTE LATER (° C.) | HEAT INSULATION |
| EMBODIMENT 9 | 176 | ⊚ |
| EMBODIMENT 10 | 180 | ⊚ |

The surface temperature of the aluminum plate used for each test sample on the side opposite to the hot plate reached 200° C. after heating for 1 minute. For this reason, it can be said that when the temperature is less than 200° C. one minute after the sample to be tested, the adiabatic effect by the adhesion prevention film appears.

For the evaluation of the heat insulating property, it was evaluated that the heat insulating property was "very good" (⊚ (very good)) when the temperature of the sample to be tested was lower by 20° C. than the equilibrium temperature (200° C.) of the aluminum plate by 1° C. or more. When the temperature of the test sample was 1 minute lower than the equilibrium temperature of the aluminum plate by 5° C. or more but less than 20° C., the heat insulating property was evaluated as "good" (o good). When the temperature of the test sample was 1 minute lower than the equilibrium temperature of the aluminum plate by 0° C. or more but less than 5° C., the heat insulating property was evaluated as "poor" (x (no good)).

[Heat Insulation Property Evaluation Results]

As shown in Table 5, the temperatures after 1 minute in Examples 1 to 6 were 188° C., 192° C., 188° C., 191° C., 192° C. and 190° C., respectively. The heat insulating properties of Examples 1 to 6 were judged to be "good" (indicated as "o" in Table 5).

The temperatures after 1 minute in Examples 7 to 10 were 170° C., 178° C., 176° C. and 180° C., respectively. The heat insulating properties of Examples 7 to 10 were judged to be "very good" (described as "⊚" in Table 5).

In Examples 7 to 10, the first conductive particles are composed of the first conductive particles in which the thin metal layer 15b is formed on the nonconductive base material 15a having poor thermal conductivity as compared with the metal material 15A. For this reason, in Examples 7 to 10, it is considered that the heat insulating property became very good. Even in the case of Example 10 having the lowest heat insulating properties among Examples 7 to 10, the temperature after 1 minute was lower by 8° C. than the temperature after 1 minute in Examples 1 and 3, which had the highest heat insulating properties among Examples 1 to 6.

In particular, Example 7 was lower by 30° C. than the equilibrium temperature of the aluminum plate. The reason for this is considered to be that a heat insulating effect by a hollow structure of hollow silica used as the base material 15a was added.

While preferred embodiments of the invention have been described and illustrated above, it should be understood that these are exemplary of the invention and are not to be considered as limiting. Additions, omissions, substitutions, and other modifications can be made without departing from the scope of the present invention.

Also, the invention is not to be considered as being limited by the foregoing description, and is only limited by the scope of the appended claims.

According to each of the embodiments described above, it is possible to provide an adhesion prevention film that can improve adhesion prevention performance of a biological tissue even when used for medical devices that releases high-frequency power to a biological tissue, and to provide a medical device that can improve adhesion prevention performance of a biological tissue.

What is claimed is:

1. A medical device comprising:
an electrode; and
an adhesion prevention film provided on a surface of the electrode, the adhesion prevention film comprising:
one or more layers;
wherein an outermost layer of the one or more layers contains a resin with a continuously usable temperature of at least 200° C., and a plurality of conductive particles;
wherein a surface of the outermost layer is provided with recesses and projections formed by some of the plurality of conductive particles being exposed from the resin;
wherein the plurality of conductive particles include:
a first conductive particle group having a median diameter that is in a range of from 1 µm to 20 µm; and
a second conductive particle group having a median diameter that is in a range of 0.01 µm to 0.5 µm; and
wherein particles in the first conductive particle group and the second conductive particle group are provided in the outermost layer in amounts such that the outermost layer has electrical conductivity.

2. The medical device according to claim 1, wherein the resin includes one or more resins selected from a group consisting of a silicone resin, a furan resin, a polyamide resin, an allyl resin, a polyimide resin, a PEEK resin, and an epoxy resin.

3. The medical device according to claim 1, wherein the resin is a silicone resin.

4. The medical device according to claim 1, wherein the recesses and projections on the surface of the outermost layer provide the surface of the outermost layer with unevenness having a maximum height Rz (Sz) of at least 0.3 µm.

5. The medical device according to claim 1, wherein the first conductive particle group includes composite particles having a particulate base material composed of a nonconductor and a metal layer formed on a surface of the base material.

6. The medical device according to claim 1, wherein the plurality of conductive particles includes composite particles having a particulate base material composed of a nonconductor and a metal layer formed on a surface of the base material.

7. The medical device according to claim 1, wherein the plurality of conductive particles includes one or more metals selected from a group consisting of silver, platinum, copper, nickel, and gold.

8. The medical device according to claim 1, wherein the one or more layers are a plurality of layers including the outermost layer and a lowermost layer which contains silica as a main component and provided on a lower layer side of the outermost layer.

9. The medical device according to claim 1, wherein the medical device is configured to apply a high frequency voltage to living tissue via the electrode.

10. The medical device according to claim 1, wherein the first conductive particles and the second conductive particles provide electrically conductive paths through the outermost layer.

* * * * *